(12) United States Patent
Ramirez et al.

(10) Patent No.: US 8,999,356 B1
(45) Date of Patent: Apr. 7, 2015

(54) DRUG DELIVERY SYSTEM

(75) Inventors: Jose E. Ramirez, Trumbull, CT (US); Austin McNamara, Villa Park, CA (US); Judy Hattendorf, Marina Del Ray, CA (US); Steve Goldner, Farmington Hills, MI (US)

(73) Assignee: OMP, Inc., Irvine, CA (US)

( * ) Notice: Subject to any disclaimer, the term of this patent is extended or adjusted under 35 U.S.C. 154(b) by 2405 days.

(21) Appl. No.: 11/291,234

(22) Filed: Dec. 1, 2005

Related U.S. Application Data

(60) Provisional application No. 60/633,407, filed on Dec. 3, 2004.

(51) Int. Cl.
*A61K 8/02* (2006.01)
*A61K 9/06* (2006.01)

(52) U.S. Cl.
CPC ........................................ *A61K 9/06* (2013.01)

(58) Field of Classification Search
USPC .......................................................... 424/401
See application file for complete search history.

(56) References Cited

U.S. PATENT DOCUMENTS

| | | | |
|---|---|---|---|
| 2,376,884 A | 5/1945 | Schwenk et al. | |
| 2,377,188 A | 5/1945 | Schwenk et al. | |
| 3,755,560 A | 8/1973 | Dickert et al. | |
| 3,856,934 A | 12/1974 | Kligman | |
| 4,136,166 A | 1/1979 | Barnett et al. | |
| 4,229,427 A | 10/1980 | Whitehouse | |
| 4,421,769 A | 12/1983 | Dixon et al. | |
| 4,466,955 A | 8/1984 | Calvo et al. | |
| 4,526,779 A | 7/1985 | Hashimoto | |
| 4,792,443 A | 12/1988 | Filomeno | |
| 5,143,763 A | 9/1992 | Yamada et al. | |
| 5,523,077 A | 6/1996 | Pawelek et al. | |
| 6,497,860 B1 | 12/2002 | Kawato et al. | |
| 6,699,464 B1 | 3/2004 | Popp et al. | |
| 2004/0052741 A1 | 3/2004 | Wortzman et al. | |
| 2004/0185016 A1 | 9/2004 | Popp et al. | |
| 2004/0191330 A1* | 9/2004 | Keefe et al. | 424/638 |

FOREIGN PATENT DOCUMENTS

| | | |
|---|---|---|
| EP | 0 688 204 B1 | 12/1995 |
| WO | WO 01/85102 A2 | 11/2001 |

OTHER PUBLICATIONS

1995 U.S. Pharmacopeia/National Formulary USP 23/NF 18, pp. 769-770 and 1572-1573.
*Cosmetic/Personal Care Packaging. Containers.* http://www.cpcpkg.com, Oct. 22, 2004.
Tina S. Alster, "Combined Laser Resurfacing and Tretinoin Treatment of Facial Rhytides", *Cosmetic Dermatology*, vol. 10, No. 11, pp. 39-42 (Nov. 1997).
Nicholas Lowe, "Understanding How Topical Retinoids Work", *Skin & Aging*, pp. 39-42 (Feb. 1999).
Olsen, et al. "Tretinoin Emollient Cream for Photodamaged Skin: Results of 48-Week, Multicenter, Double-Blind Studies", *Journal of the American Academy of Dermatology*, pp. 217-226 (Aug. 1997).
Green, et al. "Photoaging and the Skin", *Dermatologic Clinics*, vol. 11, No. 1 pp. 97-105 (Jan. 1993).
Buka et al. "How to use Retinoids to Prevent Skin Cancer and Treat Photoaging", *Skin & Aging*, pp. 32-39 (Jun. 1999).
Brochure—The Science of Skin Health Restoration—Nu-Derm System (2000).
Photo of Obagi Nu-Derm™ Toner I™, back image (1997).
Photo of Obagi Nu-Derm™ Toner II™, front and back images (1995).
Photo of Obagi Nu-Derm™ Cleanser II™, front and back images (1997).
Photo of Obagi Nu-Derm™ Clear™, front and back image (1997).
Photo of Obagi Nu-Derm™ Exfoderm™, front and back image (1997).
Photo of Obagi Nu-Derm™ Action™, front and back image (1999).
Insert, Obagi Medical Products, Inc., Long Beach, CA 90502 (2000).

* cited by examiner

*Primary Examiner* — Robert A Wax
*Assistant Examiner* — Melissa Mercier
(74) *Attorney, Agent, or Firm* — Kilpatrick Townsend & Stockton LLP

(57) ABSTRACT

Drug delivery systems and a treatment regimen that improves percutaneous absorption of topically applied drug or active agent is described. The method generally has three steps including pre-treating the surface of skin in need thereof; applying an active ingredient to the skin; and applying a post treatment agent to the skin. Pre-treatment agents, drugs and active ingredients, as well as post treatment agents are described.

15 Claims, No Drawings

000# DRUG DELIVERY SYSTEM

RELATED APPLICATION

This Application claims priority benefit of U.S. Provisional Application No. 60/633,407 filed Dec. 3, 2004 herein incorporated by reference in its entirety.

BACKGROUND

1. Technical Field

This disclosure relates to topical drug delivery systems. More particularly, treatment regimens that improve percutaneous absorption of an active ingredient are described. The methods generally include pre-treating the skin to render the epidermal area more receptive to the application of a drug or active ingredient thereto; applying one or more drugs or other active ingredients to the pre-treated area; and applying a post-treatment to the treated area.

2. Background of the Invention

The topical application of active ingredients to improve skin characteristics rarely, if ever attains the maximum benefit possible. The condition of the skin to which the active is applied may diminish the effectiveness of the active. For example, the condition of the skin may cause degradation of the active requiring application of unnecessarily large amounts of the active ingredient and of potentially irritating degradation by-products to the skin. Furthermore, varying skin characteristics such as hygiene, skin moisture content, and pH may diminish the effectiveness of the active ingredient. Moreover, the abilities of certain drugs to maintain contact with the skin once applied may further diminish the effectiveness of the active ingredient. Together, these factors may significantly decrease the effectiveness of active ingredient resulting in the need for frequent and/or prolonged application of the active to obtain a desired beneficial effect.

The prior art is problematic in that it does not demonstrate improving percutaneous absorption of an active ingredient by preparing skin for the immediate penetration of drug or active ingredient while ensuring that the drug and active ingredients maintain contact with the skin. Accordingly, there remains room for improvement in skin treatment regimens that improve percutaneous absorption of an active ingredient in skin in need of treatment.

SUMMARY

Methods in accordance with embodiments of the present disclosure involve specific steps in a skin therapy or treatment system that can be better than the individual steps performed alone. The skin treatment system in accordance with this disclosure includes the sequential steps of pre-treating the skin to render the area more receptive to the application of a drug or active ingredients thereto; applying one or more drugs or other active ingredients to the pre-treated area, and post-treating the treated area.

The present disclosure further relates to a method which includes the step of applying one or more pre-treatment agents to an area of skin in order to actively enhance penetration of the active ingredients, and/or enhances long term penetration of one or more drugs or active ingredients. In embodiments, the present disclosure relates to applying a post-treatment agent to the pre-treated/treated skin to keep the active ingredient in contact with the skin for a longer duration than application of the active ingredient without post-treatment. The present methods may result in an increase in the presence of an active ingredient in two levels of the skin (i.e., the epidermis, and dermis), compared to application of the active ingredient alone.

DETAILED DESCRIPTION OF PREFERRED EMBODIMENTS

Treatment regimens in accordance with this disclosure include the sequential steps of: pre-treating the surface of skin in need thereof; applying an active ingredient to the skin; and optionally applying a post-treatment agent to the skin, wherein the percutaneous absorption of the active ingredient is increased compared to application of the active ingredient to untreated skin.

The first step of the present method is pre-treatment. The pre-treatment step of the treatment regimen of the present disclosure is designed for rendering the area of skin to be treated more receptive to the application of the drug(s) or active ingredients thereto. For example, skin that is overly hydrated, excessively dry, keratinized, oily, dirty, basic or acidic can be pre-treated to a healthier more hygienic neutral state. It has been found that cleaning, toning, moisturizing, exfoliating, vasodilating, pore opening and/or dehydrating skin actively promotes penetration of drugs and active ingredients applied to the skin surface.

Materials suitable for use as pre-treatment agents include preparatory compositions pre-selected to clean, tone, moisturize, neutralize, exfoliate, vasodilate, dehydrate, hydrate, or open the pores of skin in need of treatment. Non-limiting examples of preparatory compositions are listed below and include cleanser compositions, toner compositions, exfoliants, vasodilators, and pore opening compositions. Other suitable preparatory compositions include moisturizers and drying agents. The preparatory compositions are categorized in various classes however this classification is not intended to limit the preparatory compositions in any way to only to those preparatory compositions belonging to the categories herein mentioned. Moreover, as described below, the same or different preparatory compositions may be used as post treatment agents in accordance with the present disclosure.

Preparatory Compositions

In accordance with the present disclosure, cleanser compositions can be applied to skin in amounts that provide the benefit to the skin of the user, such as in an amount sufficient to remove dirt and oil from the skin. Generally, the cleansers are soap-free and include water, detergent, surfactant, humectants, skin conditioning agent, PH adjustor, extracts, preservatives, fragrance and colorant, however, any cleanser suitable for removing dirt and oil from skin may be used. Suitable cleansers are commercially available and typically include a combination of anionic, cationic, amphoteric and/or non-ionic surfactants in an aqueous vehicle. The cleanser advantageously can include a combination of compounds to compensate for the well known fact that cleansing agents, by their very nature, are not always well tolerated by the skin. The oil-removal feature of a cleanser can result in drying of the skin, and skin irritation. By incorporating various protective agents in the cleanser process the cleanser overcomes shortcomings found in many alternative products. One commercially available preparatory composition is Obagi Nu-Derm® cleanser from OMP, Inc. of Long Beach, Calif. The Obagi Nu-Derm® cleanser contains a combination of water, cocamidopropyl betaine, sodium lauroyl oat amino acids, sodium laureth sulfate, glycerin, aloe barbadensis gel, glycerth-7, apricot triethanolamine, sage extract, borage extract, phenoxythanol, methylparaben, propylparaben, ethylparaben, butylparaben, saponins, fragrance, and colorant.

Optionally, foaming gel may be applied in amounts that provide the benefit to the skin of the user, such as in an amount sufficient to remove dirt, oil and/or impurities to clean skin and leave it more receptive to treatment. Generally, foaming gels include water, detergent, surfactant, humectants, skin conditioning agent, PH adjustor, extracts, preservatives, fragrance and colorant; (however any foaming gel may be applied that cleans the skin by removing dirt and/or oil). One commercially available composition is Obagi Nu-Derm® foaming gel from OMP, Inc. of Long Beach, Calif. The Obagi Nu-Derm® foaming gel contains a combination of water, sodium lauryl oat amino acids, cocamidopropyl betaine, sodium laureth sulfate, aloe barbadensis gel, alfalfa extract, borage extract, sodium chloride, xantham gum, saponins, phenoxythanol, methylparaben, propylparaben, ethylparaben, butylparaben, fragrance and colorant. This cleanser frees the skin of pollutants without damaging the skin's own natural moisture content.

Optionally, toner may be applied in amounts that provide the benefit to the skin of the user, such as in an amount sufficient to hydrate and tone skin while reducing the pH of the skin. Toner also helps by removing dirt, oils, and grime without overly drying out sensitive skin. Generally, toners include water, skin conditioner, astringent, minerals, moistening agent, vitamins and complexes thereof, anti-microbial, cleanser, extract, surfactant, anti-irritant, fragrance and colorant; however any commercially available skin toner may be used. One commercially available composition is Obagi Nu-Derm® toner available from OMP, Inc. of Long Beach, Calif. to ameliorate the potentially harsh or drying effects of witch hazel. The Obagi Nu-Derm® toner contains a combination of water, aloe barbadensis gel, witch hazel distillate, potassium alum, sodium PCA, panthenol, DMDM hydantion, polysorbate 80, allantoin, sage extract, calendula officinalis extract, saponins, fragrance, and colorant.

Optionally, exfoliant may be applied in amounts that provide the benefit to the skin of the user, such as in an amount sufficient to remove impurities and dead skin cells from the surface of skin that clog pores and make skin look dull, such as by removing flakes or scales or peeling a layer of skin. Exfoliants typically work by stimulating new growth of skin and collagen by decreasing the bond that holds dead skin cells on the surface. This allows dead cells to be removed gradually, leaving behind a layer of smoother and softer skin. Typically, the exfoliant is applied to the face, neck, hands, chest, legs, and arms, in amounts sufficient to promote circulation, improve skin texture and inhibit breakouts.

Suitable exfoliants for use with the methods of the present disclosure are commercially available, and include glycolic acid, lactic acid, and salicyclic acid. Because of its small molecular size, glycolic acid is suitable for cosmetic use. Penetration of the epidermis' cells occurs best with glycolic acid when compared to the effectiveness of other alpha-hydroxy agents. Glycolic acid decreases the adhesion between cells causing them to separate and shed more rapidly and provides a rejuvenating effect in the treatment of dry rough skin. The strength (and pH) of the glycolic acid may vary, depending on the application, such as between 70% glycolic acid (pH 0.6), 50% (pH 2.0), 40% (pH 2.2), and 30% (pH 2.3).

Another suitable exfoliant is lactic acid. However, lactic acid has the benefit of being milder than other exfoliants, so people with sensitive skin can apply lactic acid to obtain results similar to stronger acids. For example, people suffering from rosacea, a common skin condition characterized by redness, pimples, and broken blood vessels, may use lactic acid exfoliant rather than glycolic acid because the mild exfoliating acid is less irritating.

Exfoliants in accordance with the present disclosure are suitable for use in the treatment of, among other things: acne, acne scars, blackheads, dry and sun-damaged skin, blotchy pigmentation, fine wrinkles, loss of elasticity, large pores, bumps, age spots/dark spots, eczema, seborrheic keratosis, hyperkeratosis, and actinic keratosis. Accordingly exfoliants may be pre-selected for use in treating the above skin conditions.

The commercially available Obagi Nu-Derm® Exfoderm and Obagi Nu-Derm® Exforderm Forte may be used as exfoliants in accordance with the present disclosure.

Suitable exfoliant compositions are available as creams, lotions, emulsions, colloids, gels or the like, and may include inert as well as additional active ingredients for topical application.

Optionally, vasodilators may be applied to skin in amounts that provide the benefit to the skin of the user, in an amount sufficient to make blood vessels widen (i.e., dilate). Vasodilators increase blood flow bringing more oxygen and nutrients to the skin, while allowing more debris and waste to be removed.

Non-limiting examples of suitable vasodilators include any drug or active ingredient that can vasodilate including antihypertensives, prostaglandins and vitamins. Non-limiting examples further include: amyl-nitrate, diazoxide such as Hyperstat®, hydralizine such as Apresoline®, hydralazine/hydrochlorothiazide/reserpine such as Ser-Ap-Es®, and Hydralazine/hydrochlorothiazide such as Apresazide®, minoxidil (Loniten®), bradykinin (a peptide of the kinin group of proteins which causes contraction of non-vascular smooth muscle), Niacin, 1,2,3-trinitrooxypropane such as Nitrospan, nitroglycerin such as Nitrostat®, amlodipine such as Norvasc, pentaerythritol such as Peritrate, and prostaglandins such as Prostacyclin (PGI2).

Other suitable vasodilator preparatory compositions include "natural" vasodilators which cause the production of nitric oxide. Among the natural vasodilators are L-Arginine HCL (an amino acid found in dietary products), menthol USP (a compound obtained from mint oils), and silver micronutrient for stimulating glands and the endocrine system. It is believed that an enzyme converts L-Arginine to nitric oxide, which brings more blood to the treatment area. In embodiments, a commercially available cream known as Befar® incorporates the vasodilator alprostadil into the treatment regimen.

Some suitable essential oils have suitable vasodilation properties such as clary sage, geranium, fennel, lemongrass, lavender, rosemary, and carrot.

Suitable vasodilator compositions are available as creams, lotions, emulsions, colloids, gels or the like, and may include inert as well as additional active ingredients for topical application.

Optionally, pore opening compositions may be applied in amounts that provide the benefit to the skin of the user, such as in an amount sufficient to increase the size of the pores of the user.

Suitable pore opening compositions include benzoyl peroxide, sulphur, topical antibiotics, resorcinol, retinoic acid, tretinoin used alone or in combination with beta hydroxyl and alpha hydroxyl acids. Other suitable beta hydroxyl acids include salicylic acid.

Suitable retin-A compositions are applied in amounts sufficient to open pores, such as medically prescribed tretinoin. Tretinoin skin preparations are a family of drugs all similar to Vitamin A. Tretinoin is used to treat acne and aged, sun damaged skin. Tretinoin works best when used in combination with alpha hydroxyacid preparations. The inclusion of tretinoin stimulating composition in the treatment regimen is important in keratinocyte activity regulation, mitosis, repairing damaged DNA, blood vessel formation such as angiogenesis, pore opening, and the creation of a soft epidermis. Furthermore, the use of Retin-A such as tretinoin helps make the skin healthier and addresses dysfunctional skin conditions such as acne, hyperpigmentation and photoaging.

Pore opening compositions are available in topically applied compounds such as creams, lotions, emulsions, colloids, gels, liquids and the like which can be applied at room temperature by any suitable means and which can be deposited on to the area to be treated.

As noted above, in practicing the present methods, the preparatory compositions for the pre-treatment can be preselected according to the drug and the type of treatment to be effected to the localized area. For example, if it is desired that the type of drug to be applied is for an acne infected area, then, an exfoliant preparatory composition could be used. Similarly, if the type of drug to be applied is for treating an acute pain, then a vasodilator or a pore opening preparatory compound would be applied as the pre-treatment. Furthermore, if it is desired that the type of drug to be applied is for a rosacea area, then, a mild exfoliant preparatory composition could be used.

Thus, the pre-treatment composition is pre-selected according to the type of drug to be applied to the area to be treated. Other pre-selection factors include the type of skin to be treated, the original presentation of the skin, the type of disease or sickness to be treated, and combinations of these factors.

Drugs and Active Ingredients

In accordance with the present disclosure, pre-treated skin can also be treated by applying one or more active ingredients to the skin. Suitable topically applied drugs or pharmaceutical ingredients are well known and commercially available. Such compositions include active and inactive ingredients which stabilize and maintain the pharmaceutical or drug composition within the formulation.

Non-limiting examples of drug or active agents which may be applied to the pre-treated skin are listed below. The drugs and active ingredients are applied in amounts that provide a benefit to the skin of a user. While the amount of active used will depend on a number of factors including the specific active chosen and the benefit to be achieved, generally, amounts from about 0.01 to about 10% by weight of the total composition is suitable. In embodiments, the active is present in an amount from about 0.1 to about 5% by weight of the total composition.

Suitable drugs or active ingredients are categorized in various classes however this classification is not intended to limit the actives in any way to only those actives belonging to the categories herein mentioned.

Antimicrobial Actives

Antimicrobials which may be applied to a pre-treated area of skin include all antibiotics, antimicrobial agents and antimicrobial peptides. Antibiotics that may be used include inter alia dermatologically acceptable salts of tetracycline and tetracycline derivatives, gentamycin, kanamycin, streptomycin, neomycin, capreomycin, lineomycin, paromomycin, tobramycin, erythromycin, triclosan, octipirox, parachlorometa xylenol nystatin, tolnaftate, miconazole hydrochloride, chlorhexidine gluconate, chlorhexidine hydrochloride, methanamine hippurate, methanamine mandelate, minocycline hydrochloride, clindamycin, cleocin, b-lactam derivatives such as aminopenicillin and mixtures thereof. One embodiment for use herein includes chlorhexidine gluconate and triclosan.

Antimicrobial agents that may be used in accordance with the present disclosure either alone or in combination include for example benzoyl peroxide and salicylic acid.

Antimicrobial peptides useful herein are for example magainin, nicin, and cecropin.

Anti-Acne Actives

Anti-acne actives which may be applied to a pre-treated area of skin include all known anti-acne compounds. Anti-acne actives include without limitation keratolytic agents including lactic acid, pyruvic acid, salicylic acids, urea and N-acetylcysteine; retinoids, and retinoid analogs such as tretinoin, cis and trans retinoic acid, retinol and retinol palmitate, isotretinoin-13-cis-retinoic acid; antibiotics and antimicrobial agents such as tetracycline, erythromycin, minocycline, clindamycin, trimethoprim-sulphamethazole and anti-microbial peptides (nicin, for example); steroids, such as hydrocortisone; gamma-linolenic acid and mixtures thereof. Further anti-acne actives that may be used include without limitation benzoyl peroxide; alpha and beta hydroxy acids; sulfacetamide and sulfur and mixtures thereof. Other actives used herein are salicylic acid, and retinoids.

Anti-Psoriasis Actives

Anti-psoriasis actives which may be applied to a pre-treated area of skin include all known anti-psoriasis compounds. Anti-psoriasis actives for use in accordance with the present disclosure include without limitation salicylic acid; mometasone furoate; steroids including corticosteroids such as cortisone and oluxclobetasol propionate; 5-fluorouracil; epinephrine; anthralin; vitamin D3 analogs, such as calcipotriene; methotrexate; masprocol; trimethaxate gluconate; retinoids; cyclosporin; paclitaxel; 5-amino levulinic acid; bergasol; tin-ethyl etio purpurin; benzoporphyrin derivatives; antibodies, such as ABX-IL8 antibody, CD11a monoclonal antibody and ICM3 monoclonal antibody; enzyme inhibitors, including tryptase inhibitor and phospholipase A-2 inhibitors; angiogenesis blocking agents; T-cell blocking agents and mixtures thereof.

Anti-Eczema Actives

Anti-eczema actives which may be applied to a pre-treated area of skin include all known anti-eczema compounds. Anti-eczema actives useful herein include urea; evening primrose oil; plant extracts; hydrocortisone; an immunomodulator; tar combined with fatty acids obtained from banana; and mixtures thereof.

Topical Anesthetic Actives

Topical anesthetic actives for use with the present disclosure include tetracaine, lidocaine, editocaine, bupivacaine, pramoxine; and mixtures thereof.

Anti-Inflammatory Actives

Antiinflammatory actives for use in accordance with the present disclosure include steroidal actives such as hydrocortisone as well as non-steroidal actives including propionic derivatives; acetic acid derivatives; biphenylcarboxylic acid derivatives; fenamic acid derivatives; and oxicams. Examples of antiinflammatorty actives include without limitation acetaminophen, oxaprozin, pranoprofen, benoxaprofen, bucloxic acid, elocon; and mixtures thereof.

Vitamin Actives

Vitamin actives for use in accordance with the present disclosure include vitamin A and derivatives, including retinoic acid, retinyl aldehyde, retin A, retinyl palmitate, adapalene, and beta-carotene; vitamin B (panthenol, provitamin B5, panthenic acid, vitamin B complex factor); vitamin C (ascorbic acid and salts thereof) and derivatives such as ascorbyl palmitate; vitamin D including calcipotriene (a vitamin D3 analog) vitamin E including its individual constituents alpha-, beta-, gamma-, delta-tocopherol and cotrienols and mixtures thereof and vitamin E derivatives including vitamin E palmitate, vitamin E linolate and vitamin E acetate; vitamin K and derivatives; vitamin Q (ubiquinone) and mixtures thereof.

Protein Actives

One class of actives for use in accordance with the present disclosure are proteins and peptides. In principle, any desired protein or peptide may be produced using this technology and oil bodies comprising these recombinant proteins may be incorporated in the emulsions of the present disclosure. Proteins and peptides which may be used in accordance with the present disclosure include enzymes such as proteases (e.g. bromelain, papain, collagenase, elastase), lipases (e.g. phospholipase C), esterases, glucosidases, exfoliating enzymes; antibodies and antibody derived actives, such monoclonal antibodies, polyclonal antibodies, single chain antibodies and the like; reductases; oxidases; peptide hormones; natural structural skin proteins, such as elastin, collagen, reticulin and the like; growth factors such as platelet derived growth factor (PDGF) and epidermis derived growth factor (EGF); anti-oxidants such as superoxide dismutase, catalase and glutathione; free-radical scavenging proteins; DNA-repair enzymes, for example T4 endonuclease 5 and P53; antimicrobial peptides, such as magainin and cecropin; a milk protein; a silk protein or peptide; and any active fragments, derivatives of these proteins and peptides; and mixtures thereof.

Anti-Wrinkle and Anti-Aging Actives

Anti-wrinkle and anti-aging actives for use in accordance with the present disclosure include without limitation hydroxy acids including $C_2$-$C_{30}$ alpha-hydroxy acids such as glycolic acid, lactic acid, 2-hydroxy butanoic acid, malic acid, citric acid tartaric acid, alpha-hydroxyethanoic acid, hydroxycaprylic acid and the like; beta hydroxy acids including salicylic acid and polyhydroxy acids including gluconolactone (G4); and mixtures of these acids. Further anti-wrinkle agents include retinoic acid, gamma-linolenic acid; fruit acids, sugar cane extract and glycomer in cross-linked alpha nutrium; and mixtures thereof. Skin peel agents for example phenol, phytic acid and acetic acid may also be used in accordance with the present disclosure. Salicylic acid, lactic acid and glycolic acid are also for use herein.

Whitening and Bleaching Actives

Whitening and bleaching agents include kojic acid, lactic acid, ascorbyl acid and derivatives such as magnesium ascorbyl phosphate; arbutin; hydroquinone, and licorice root.

Sunless Tanning Actives

Sunless tanning actives include dihydroxyacetone (DHA); glyceryl aldehyde; tyrosine and tyrosine derivatives such as malyltyrosine, tyrosine glucosinate, and ethyl tyrosine; phospho-DOPA, indoles and derivatives; and mixtures thereof.

Non-Steroidal Drugs

Other useful drugs include non-steroid drugs for releasing pain and include, for example, ketoprofen, fellinac, ibuprofen, pirorican, bis(indole) alkaloid compounds and the like.

Miscellaneous Active Ingredients

Further active ingredients for use in accordance with the present disclosure include an amino acid and amino acid derivative; an insect repellant; a fungicide (such as ketoconazole, itraconazole, saperconazole); an anti-viral agent (such as acyclovir); an anti-cancer agent; a plant extract; an anti-hemorrhoid compound; an anti-dandruff compound; a hair-growth stimulating compound such as minoxodil and Revivogen; a hair loss stimulating compound; a nucleic acid (DNA, RNA and derivatives); an anti-scabies agent (such as permethrin); an anti-wart agent (such as podophyllotoxin); and mixtures thereof.

Thus compositions for use in accordance with the present disclosure include bacitracin, cortisone-containing compositions; antibiotics, such as Neosporin; hydroquinone; antibacterial compositions; gastrointestinal drugs; anti-fungal drugs; addiction modifiers; cardio-vascular, cardio-pulmonary and pulmonary treatment drugs; anti-inflammatory compounds; hypo-allergenic compounds, analgesic compounds, hypertension treatment drugs; diabetes treatment drugs or pharmaceutical compounds, neurological treatments and the like, as well as sequential applications thereof, and the like. Antibiotics such as nicotinamide, clindamycin and erythromycin can be topically applied in treating acne. Other useful antibiotics and drugs include, for example, 5F-U for treating certain types of cancer, minoxidil, and the like.

Ordinarily, the pharmaceutical or drug composition is compounded into a formulation suitable for topical application which can be directly applied to the localized to be treated. Topical antibiotics tend to dry and irritate the skin and require proper cleansing and moisturizing. Therefore such compositions, as well as the other pharmaceuticals, ordinarily, include emollients, surfactants, fatty acids such as lanoleic acid, polyhydric compounds such as glycerin, fragrances, and the like. Usually, the active ingredient is present in the composition in an amount from about 0.01% to about 10%, by weight based upon the total weight of the composition. As noted, compositions are usually homogeneous compositions which can be directly applied to the area to be treated and remain thereon until removed therefrom.

The treatment regimens in accordance with the present disclosure are useful for delivering topical anesthetics, in addition to the vasodilators. Anesthetics useful herein as well as other enumerated vasodilators can be found in U.S. Patent Application Publication No. 2002/0006435, published Jan. 17, 2002 (the entire disclosure of which is incorporated herein by this reference). Also, enhancers for promoting the transdermal delivery of pharmaceutical agents, such as found in U.S. Pat. No. 6,019,997 (the entire disclosure of which is incorporated herein by this reference), and Patent Application Publication No. U.S. 2004/0013747 (the entire disclosure of which is incorporated herein by this reference).

Post-Treatment

The next step in the treatment regimen is applying a post-treatment agent to the pre-treated/treated skin. Typically, the type of treatment applied to the skin treatment area will dictate the type of post-treatment to be applied to the dermal layer. Thus, the post-treatment can include encapsulating the drug, or repeating the pre-treatment step with the same or different pre-treatment agents, or repeating the treatment step with the same or different drugs or active ingredients. Accordingly, the selection of a post-treatment agent is determined by the type of drug delivered, or treatment desired.

It should be noted that a post-treatment composition, as well as the drug, itself, and the pre-treatment can comprise not just a single application of a single selected compound but can be a sequentially applied treatment. For example, multiple exfoliants can be used as well as multiple drug applications and sequential post-treatments. Thus the classification as a post-treatment agent is not intended to limit the post-treatment agents in any way to only those post treatment agents mentioned herein. Thus suitable post-treatment agents keep the active in contact with the skin for a longer duration and include any preparatory composition mentioned herein or active ingredient described above.

Other suitable post-treatment compositions may be formulated in a suitable ointment capable of encapsulating an active ingredient on skin, including, but are not limited to, mineral oil, petrolatum compound, liquid petrolatum, white petrolatum, propylene glycol, polyoxyethylene, polyoxypropylene compound, emulsifying wax, etc. Other suitable post-treatment compositions are selected according to the actual treatment and whether the drug or active ingredient remains on the treated site, is fully absorbed, or flows away from the pre-treated/treated skin. Other suitable post-treatment agents include occlusive emollient compounds, petrolatum, water-in-oil emulsions, and/or similar products, and combinations of these post-treatment agents.

The following examples illustrate aspects and features of a specific implementation in accordance with the present disclosure. It should be understood the following is representative only, and that the disclosure is not limited by the detail set forth in this example.

Example I

An 18 year old male is presented with acne or pimples exacerbated by plugged-up skin pores. Oil production in the sebaceous glands (sebum) is filling up pores inside the facial skin cells and sealing them on the surface. More solid skin debris (keratin) is being produced and plugging the pore opening. Skin is cleaned with a foaming gel, toner, and/or exfoliant and treated with topical erythromycin, and post-treated with post-treatment of foaming gel, toner, and tretinoin in order to cover the pre-treated/treated area.

Example II

An in-vitro study of percutaneous absorption of vitamin C formulation in human cadaver skin is conducted. In the study vitamin C compositions are applied to different cadaver skin samples. The following application protocols are used on the different groups of skin cells:
Treatment A. 20% vitamin C composition is applied to human cadaver skin samples.
Treatment B. Obagi Nu-Derm® cleanser, toner, and 20% vitamin C composition is applied to human cadaver skin samples. Appropriate time is allowed for the skin to dry. Occlusive emollient compound, petrolatum, water-in-oil emulsion and/or similar product is smeared over the treated area and allowed to remain for a suitable period of time.

Percutaneous absorption of Vitamin C in Treatment B is expected to be greater than that of Treatment A.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method of improving the percutaneous absorption of an active ingredient topically applied to the skin of a user, the method comprising:
    pre-treating the surface of skin;
    applying an active ingredient to the skin; and
    post-treating the skin, wherein post-treating includes applying one or more pre-treatment agents selected from the group consisting of cleansers, foaming gels, toners, exfoliants, vasodilators, pore opening compositions, and combinations thereof to the surface of the skin and wherein the percutaneous absorption of the active ingredient is increased compared to application of the active ingredient alone.

2. The method of claim 1 wherein the step of pre-treating the surface comprises applying a preparatory composition to the surface.

3. The method of claim 2 wherein the preparatory composition comprises cleanser, foaming gel, toner, exfoliant, vasodilator, pore opening composition, or combinations thereof.

4. The method of claim 3 wherein the exfoliant comprises glycolic acid, lactic acid, salicylic acid or combinations thereof.

5. The method of claim 3 wherein the pore opening composition comprises benzoyl peroxide, sulphur, resorcinol, retinoic acid, tretinoin, beta hydroxyl acids, alpha hydroxyl acids, salicylic acid, or combinations thereof.

6. The method of claim 3 wherein the vasodilator composition comprises amyl-nitrate, diazoxide, hydralizine, hydralazine/hydrochlorothiazide/reserpine, hydralazine/hydrochlorothiazide, minoxidil, bradykinin, niacin, 1,2,3-trinitrooxypropane, nitroglycerin, amlodipine, pentaerythritol, prostaglandin, nitric oxide, L-Arginine HCL, menthol, silver micronutrient, alpostadil, essential oil, or combinations thereof.

7. The method of claim 6 wherein the essential oil is selected from the group consisting of clary sage, geranium, fennel, lemongrass, lavender, rosemary, carrot, and combinations thereof.

8. The method of claim 2 wherein the preparatory composition comprises a moisturizer.

9. The method of claim 2 wherein the preparatory composition comprises a drying agent.

10. The method of claim 1 wherein the step of post-treating the skin further comprises applying a second active ingredient to the skin.

11. The method of claim 2 wherein the step of post-treating the skin comprises applying a second preparatory composition to the skin.

12. The method of claim 1 wherein the step of pre-treating the surface comprises the step of reducing the pH of the surface.

13. A method of improving the percutaneous absorption of an active ingredient topically applied to the skin of a user, the method comprising:
    applying at least one pre-treatment agent to skin;
    applying an active ingredient to treat the pre-treated skin; and
    applying at least one post-treatment agent to the treated skin, wherein the at least one post-treatment agent is the same as the at least one pre-treatment agent.

14. The method of claim 13, wherein the at least one pre-treatment agents is selected from the group consisting of cleanser, foaming gel, toner, exfoliant, vasodilator, pore opening composition, or combinations thereof.

15. The method of claim 13, further comprising applying a second active ingredient to the post-treated skin.

* * * * *

UNITED STATES PATENT AND TRADEMARK OFFICE
CERTIFICATE OF CORRECTION

| | | |
|---|---|---|
| PATENT NO. | : 8,999,356 B1 | Page 1 of 1 |
| APPLICATION NO. | : 11/291234 | |
| DATED | : April 7, 2015 | |
| INVENTOR(S) | : Ramirez et al. | |

It is certified that error appears in the above-identified patent and that said Letters Patent is hereby corrected as shown below:

On the Title Page:

Second column, in the "ABSTRACT" item (57), line 2 of the Abstract paragraph: please insert --a-- before "topically".

Second column, in the "ABSTRACT" item (57), line 3 of the Abstract paragraph: please delete "is described" and insert --are described--.

Second column, in the "ABSTRACT" item (57), lines 5-6 of the Abstract paragraph: please delete "post treatment" and insert --post-treatment--.

Second column, in the "ABSTRACT" item (57), line 7 of the Abstract paragraph: please delete "post treatment" and insert --post-treatment--.

In the Claims:

In Column 10, line 56, Claim 14: please delete "agents" and insert --agent--.

Signed and Sealed this
Third Day of May, 2016

Michelle K. Lee
*Director of the United States Patent and Trademark Office*